US005229415A

United States Patent [19]

Linn et al.

[11] Patent Number: 5,229,415

[45] Date of Patent: Jul. 20, 1993

[54] ALKYLTHIO ALKYL AVERMECTINS ARE ACTIVE ANTIPARASITIC AGENTS

[75] Inventors: Bruce O. Linn, Bridgewater; Helmut Mrozik, Matawan, both of N.J.

[73] Assignee: Merck & Co., Inc., Rahway, N.J.

[21] Appl. No.: 857,035

[22] Filed: Mar. 24, 1992

[51] Int. Cl.[5] .................... A61K 31/365; C07D 493/22

[52] U.S. Cl. ........................................ 514/450; 514/30; 536/7.1; 549/264; 549/265

[58] Field of Search ................ 549/264, 265; 514/450, 514/30; 536/7.1

[56] References Cited

U.S. PATENT DOCUMENTS

| | | | |
|---|---|---|---|
| 4,199,569 | 4/1980 | Chabala et al. | 514/30 |
| 4,200,581 | 4/1980 | Fisher et al. | 514/30 |
| 4,201,861 | 5/1980 | Mrozik et al. | 536/7.1 |
| 4,289,760 | 9/1981 | Mrozik et al. | 514/30 |
| 4,310,519 | 1/1982 | Albers-Schonbus et al. | 514/30 |
| 4,587,247 | 5/1986 | Linn et al. | 514/222 |
| 4,859,657 | 8/1989 | O'Sullivan et al. | 514/63 |
| 4,895,837 | 1/1990 | Mrozik et al. | 514/30 |
| 4,897,416 | 1/1990 | Frei et al. | 514/450 |
| 4,906,619 | 3/1990 | Eskola et al. | 514/30 |
| 5,089,489 | 2/1992 | Gibson et al. | 514/30 |

FOREIGN PATENT DOCUMENTS 2166436 5/1986 United Kingdom .

OTHER PUBLICATIONS

Projer et al., *Tetrahedron Lett.*, 35, pp. 3067-3068 (1976).

Projer et al., *Aust J. Chem.*, 31, pp. 1031-1040 (1978).

Shin et al., J. Org. Chem. 54, pp. 1459-1463 (1989).

*Primary Examiner*—Johnnie R. Brown

*Assistant Examiner*—Elli Peselev

*Attorney, Agent, or Firm*—David L. Rose; Joseph F. DiPrima

[57] ABSTRACT

Avermectin compounds are substituted at the 4″, 4′ or 13-postion hydroxy group with an alkylthioalkyl group and are optionally substituted at the other reactive positions of the avermectin molecule. The compounds are prepared by reacting protected avermectins, avermectin monosaccharides or avermectin aglycones with dialkylsulfoxides. The compounds are potent antiparasitic agents and compositions for such uses are also disclosed.

7 Claims, No Drawings

ALKYLTHIO ALKYL AVERMECTINS ARE ACTIVE ANTIPARASITIC AGENTS

BACKGROUND OF THE INVENTION

Avermectin compounds (formerly referred to as C-076 compounds) have been known for a considerable period of time as highly active antiparasitic agents in animals including humans. See U.S. Pat. No. 4,310,519 to Albers Schonberg et al., describing the isolation of the avermectin compounds from a fermentation broth. Many derivatives of avermectin compound have been prepared and described in the literature. One derivative in particular, the 22, 23 dihydro derivative has been prepared and has found considerable commercial success as antiparasitic agents against internal and external parasites of animals. That derivative is known as ivermectin and is disclosed in U.S. Pat. No. 4,199,569 to Chabala et al. Other derivatives have been described such as the 13-polyalkoxy avermectin compounds disclosed in U.S. Pat. No. 4,587,247 to Linn et al.

SUMMARY OF THE INVENTION

The instant invention is concerned with avermectin compounds substituted at the 4', 4'' or 13 position hydroxy groups with an alkylthioalkyl group. The preferred group is a methyl thiomethyl group and the compounds are potent internal and external antiparasitic agents with particularly acute activity against ectoparasites of companion animals.

DESCRIPTION OF THE INVENTION

The compounds of the instant invention are best realized in the following structural formula:

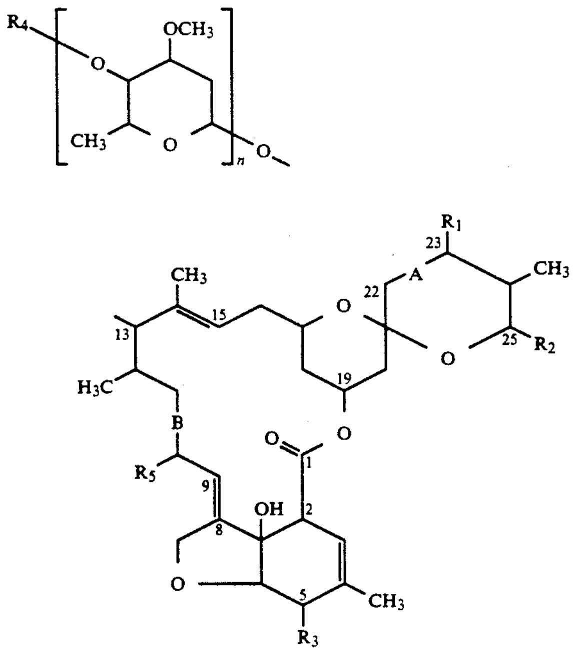

n is 0, 1 or 2;

A is single or double bond;

$R_1$ is present only when A is a single bond and is H, OH, =H, $=NOCH_3$ or halogen;

$R_2$ is $C_1$–$C_6$ alkyl, $C_2$–$C_6$ alkenyl, $C_3$–$C_8$ cycloalkyl, $C_4$–$C_8$ cycloalkenyl, phenyl, furyl or thienyl;

$R_3$ is OH or =NOH;

B is a single or double bond;

$R_5$ is present only when B is a single bond and is H, OH or halogen;

$R_4$ is

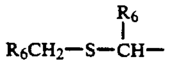

and $R_6$ is hydrogen or $C_1$–$C_3$ alkyl.

In the above formula and throughtout the instant specification of the term "halogen" is intended to include the halogens fluorine, chlorine, bromine and iodine.

Preferred compounds are realized in the above structural formula when:

n is 0, 1 or 2;

A is a single bond;

$R_1$ is H or OH;

$R_2$ is $C_1$–$C_6$ alkyl or $C_3$–$C_8$ cycloalkyl;

$R_3$ is OH;

B is a double bond;

$R_4$ is as defined above; and $R_6$ is hydrogen or methyl.

Further preferred compounds are realized in the foregoing structural formula when n is 0;

A is a single bond;

$R_1$ is H or OH;

$R_2$ is $C_3$–$C_4$ alkyl or $C_5$–$C_6$ cycloalkyl;

$R_3$ is OH

B is a double bond;

$R_4$ is as defined above; and $R_6$ is hydrogen.

Additional preferred compounds are realized in the following compounds:

13-O-Methylthiomethyl-22,23-dihydroavermectin B1 aglycone;

13-Epi-O-methylthiomethyl-22,23-dihydroavermectin B1 aglycone;

4'-O-Methylthiomethyl-22,23-dihydroavermectin B1 monosaccharide;

4'-O-Methylthiomethyl avermectin B1 monosaccharide;

13-O-Methylthiomethyl avermectin B1 aglycone;

4''-O-Methylthiomethyl-22,23-dihydroavermectin B1;

4''-O-Methylthiomethyl avermectin B1;

13-O-Methylthiomethyl-10,11,22,23-tetrahydroavermectin B1 aglycone;

13-O-Methylthiomethyl-10-hydroxy-10,11,22,23-tetrahydroavermectin B1 aglycone;

13-O-Methylthiomethyl-10-fluoro-10,11,22,23-tetrahydro avermectin B1 aglycone.

The instant compounds are prepared by reacting the 4'', 4 or 13-hydroxy group (where other reactive groups, such as hydroxy groups, are suitably protected such as by silylation) of the avermectin compound, the monosaccharide or the aglycone, respectively with a dialkyl sulfoxide, as outlined in the following reaction scheme:

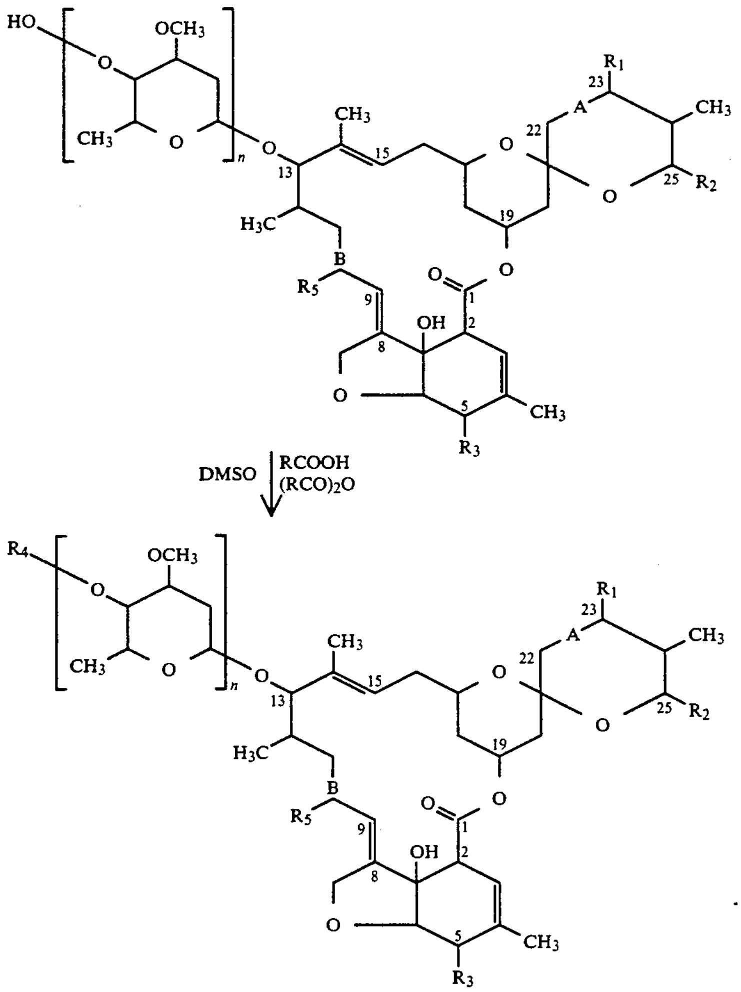

Where R is an alkyl group of 1-5 carbons.

The instant derivatives are prepared by reacting the appropriately protected avermectins, avermectin monosaccharides and avermectin aglycones or their corresponding 13-epimers wherein the 4″, 4′ or 13 posistion is hydroxy with a dialkylsulfoxide in the presence of an alkanoic acid anhydride and an alkanoic acid by the method of P. M. Pojer and S. J. Angyal, Tetrahydron Lett., 1976, 35, 3067; *Aust. J. Chem.*, 31, 1031 (1978).

One significant advantage of the alkylthioalkyl substituents over the related alkoxyalkyl substituted compounds described in U.S. Pat. No. 4,587,247 is that they are easily prepared using just a dialkyl sulfoxide, alkanoic acid anhydride and alkanoic acid reagent mixture instead of volatile and highly carcinogenic alkylating agents such as methoxymethyl chloride, which is a regulated carcinogen and can be used only in special toxic chemicals facilities.

The previously described 5-O-tert.-butyldimethylsilyl avermectins, the 5-O-tert.-butyldimethylsilyl avermectin monosaccharides and the 5-O-tert.-butyldimethylsilyl avermectin aglycones or their corresponding 13-epimers are further protected by persilylation using bis (trimethylsilyl)trifluoroacetamide in dry dimethylformamide as solvent at 60° C. for about 2 to 3 hours furnishing the corresponding 4″,7-bis-O-trimethylsilyl-5-O-tert.-butyldimethylsilyl avermectin, the 4′,7-bis-O-trimethylsilyl-5-O-tert.-butyldimethylsilyl avermectin monosaccharide and the 7,13-bis-O-trimethylsilyl-5-O-tert.-butyldimethylsilyl avermectin aglycone intermediates repectively. The trimethylsilyl groups are removed at the 4″-, 4′-or 13-positions by treating the intermediates with aqueous acetic acid in tetrahydrofuran at room temperature, for about 20 hours providing the corresponding 7-O-trimethylsilyl-5-O-tert.-butyldimethylsilyl avermectin, the 7-O-trimethylsilyl-5-O-tert.-butyldimethylsilyl avermectin monosaccharide or the 7-O-trimethylsilyl-5-O-tert.-butyldimethylsilyl avermectin aglycone intermediates.

These protected intermediates can now be alkylated with the alkylthioalkyl groups at the 4″, 4′ or 13 hydroxyl positions using an alkanoic acid anhydride and an alkanoic acid in a dialkyl sulfoxide. For example, the protected starting materials are reacted preferably with acetic anhydride and dimethylsulfoxide in the presence of glacial acetic acid at about 20° to 40° C. preferably at room temperature for several days. Preferably about 35-45 hours furnishing the O-methyl-thiomethyl-4′,4″ or 13-protected avermectin intermediate. All equipment and reagents are dried and the reaction is run under an atmosphere of dry nitrogen preferably at room temperature. The dimethyl sulfoxide is used as the solvent as well as a reagent and is usually in a ration of about 10 to 20 ml per gram of avermectin. The range at proportions of mole equivalents of dimethyl sulfoxide to glacial acetic acid to acetic anhydride is about 1:6: 1:1–4 preferably about 4:1:2. The concentration of glacial acetic acid is important. A decrease in the acid concentration below the above stated proportions causes a decrease in the yield of methylthiomethoxy product and an increase in the amount of 4″-, 4′-or 13-oxo side product. Increasing the reaction temperature about 40° C. in order to increase the reaction rate also causes a decrease in the yield of methylthiomethoxy product and an increase in the amount of oxo side product. The reaction time is from 1 to 6 days preferably about 2 days. The 13, 4′ and 4″ alkylthioalkyl protected avermectin intermediates are isolated using techniques known to those skilled in the art.

The 4″-, 4′- or 13-O-alkylthioalkyl silylated avermectin intermediates are readily desilylated under dilute acidic conditions. For example, the removal of the silyl groups of 13-O-methylthiomethyl-7-O-trimethylsilyl-5-O-tert.-butyldimethylsilyl-22,23-dihydro avermectin B1 aglycone intermediate by treatment with 0.5% methanolic para-toluenesulfonic acid monohydrate for 30 minutes at room temperature, 23° C., furnishes the 13-O-methylthiomethyl-22,23-dihydro avermectin B1 aglycone. See Linn et al—U.S. Pat. No. 4,587,247.

In this manner the 4″-, 4′- and the 13-O-alkylthioalkyl avermectins, avermectin monosaccharides and avermectin aglycones or their corresponding 13-epimers are prepared.

4″-, 4′- And the 13-O-methylthiomethyl(and other alkylthioalkyl-) avermectins, avermectin monosaccharides and avermectin aglycones or their corresponding 13-epimers, prepared as described above, are substituted in the 10 position by the method of T. L. Shih, H. Mrozik, J. Ruiz-Sanchez, *J. Org. Chem.*, 54, pg. 1459 (1989). The reaction of alkylthioalkyl avermectin with N-bromoacetamide in a 10% water: acetone solution at about 10°–40° C. preferably room temperature, for 3 to 5 hours in the dark furnishes the unstable 11-bromo-10-hydroxy-10,11-dihydro intermediate which is immediately treated with tributyltin hydride in dry toluene at 50°–100° C. preferably about 85° C. for from 1–4 hours preferably about 4 hours furnishing the alkylthioalkyl-10-hydroxy-10,11, dihydro avermectin. Protection of the 5-hydroxyl by silylation using tert.-butyldimethylsilyl chloride and imidazole in dry dimethylformamide furnished the corresponding alkylthioalkyl-10-hydroxy-5-O-tert.-butyldimethylsilyl 10,11, dihydro avermectin compound. Treatment of this intermediate with diethylaminosulfur trifluoride in dry methylene chloride at −65° C. furnishes the corresponding 10-fluoro-5-O-tert.-butyldimethylsilyl intermediate which is desilylated using hydrogen fluoride-pyridine in tetrahydrofuran for 16 hours at room temperature, providing alkylthioalkyl-10-fluoro-10,11, dihydro avermectins.

In this manner 10-hydroxy-10,11-dihydro- and 10-fluoro-10,11 dihydro- derivatives of the 4″-, 4′-and 13-alkylthioalkyl avermectins, avermectin monosaccharides and avermectin aglycones or their corresponding 13-epimers are prepared.

4″-, 4′- And the 13-O-alkylthioalkyl avermectins, avermectin monosaccharides and avermectin aglycones or their corresponding 13-epimers, prepared as described above, are hydrogenated in the 10, 11 position providing 10,11-dihydro derivatives. The alkylthioalkyl avermectin are subjected to hydrogen contained in a balloon using 5% palladium on charcol at from 10°–40° C. preferably room temperature just until the starting avermectin has completely reacted. The remaining hydrogen is immediately purged before further hydrogenation occurs. The akylthioalkyl-10,11, dihydro-compound is obtained.

In this manner the 10,11-dihydro derivatives of the 4″-, 4′- and the 13-O-alkylthioalkyl avermectins, avermectin monosaccharides and avermectin aglycones or their corresponding 13-epimers are prepared.

The preparation of additional derivatives of the various reactive substituents can also be carried out using procedures well known to those skilled in the art. See for example U.S. Pat. No. 4,906,619 to Eskola et al., for the preparation of various alkylated avermectins: U.S. Pat. No. 4,201,861 to Mrozik et al, for the preparation of various, acylated avermectins; U.S. Pat. No. 4,200,981 to Fisher et al., for the preparation of various 5-alkylated compounds; U.S. Pat. No. 4,289,760 to Mrozik et al., for the preparation of 23-keto compounds; UK Patent 2166436 for the preparation of 25-alkenyl compounds; EPO 214731 for the preparation of various 25-substituted compounds and U.S. Pat. No. 4,895,837 to Mrozik for a discussion of various procedures for the protection of avermectin compounds.

The instant compounds are potent endoand ectoantiparasitic agents against parasites particularly helminths, ectoparasites, insects, and acarides, infecting man, animals and plants, thus having utility in human and animal health, agriculture and pest control in household and commercial areas.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats, fish, buffalo, camels, llamas, reindeer, laboratory animals, furbearing animals, zoo animals and exotic species and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Habronema, Druschia, Heterakis, Toxocara, Ascaridia, Oxyuris, Ancylostoma, Uncinaria, toxascaris and Parascaris. Certain of these, such as Nematodirus, Cooperia, and Oesophagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The compounds of this invention have unexpectedly high activity against these parasites, and in addition are also active against Dirofilaria in dogs and cats, Nematospiroides, Syphacia, Aspiculuris in rodents, arthropod ectoparasites of animals and birds such as ticks, mites, lice, fleas, blowflies, in sheep Lucilia sp., biting insects and such migrating diperous larvae as Hypoderma sp. cattle, Gastrophilus in horses, and Cuterebra sp. in rodents and nuisance flies including blood feeding flies and filth flies.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunuculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., the housefly Musca domestica as well as fleas, house dust mites, termites and ants.

The compounds are also useful against insect pests of stored grains such as Tribolium sp., Tenebrio sp. and of agricultural plants such as aphids, (Acyrthiosiphon sp.); against migratory orthopterans such as locusts and immature stages of insects living on plant tissue. The compounds are useful as a nematocide for the control of soil nematodes and plant parasites such as Meloidogyne sp. which may be of importance in agriculture. The compounds are also highly useful in treating acerage infested with fire ant nests. The compounds are scattered above the infested area in low levels in bait formulations which are broght back to the nest. In addition to a direct-but-slow onset toxic effect on the fire ants, the compound has a long-term effect on the nest by sterilizing the queen which effectively destroys the nest.

The compounds of this invention may be administered in formulations wherein the active compound is intimately admixed with one or more inert ingredients and optionally including one or more additional active ingredients. The compounds may be used in any composition known to those skilled in the art for administration to humans and animals, for application to plants and for premise and area application to control household pests in either a residential or commercial setting. For application to humans and animals to control internal and external parasites, oral formulations, in solid or liquid or parenteral liquid, implant or depot injection forms may be used. For topical application dip, spray, powder, dust, pour-on, spot-on, jetting fluid, shampoos, collar, tag or harness, may be used. For agricultural premise or area application, liquid spray, powders, dust, or bait forms may be used. In addition "feed-through" forms may be used to control nuisance flies that feed or breed in animal waste. The compounds are formulated, such as by encapsulation, to lease a residue of active agent in the animal waste which controls filth flies or other arthropod pests.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the instant compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents, and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets or liquid which may then be added to the finished feed or optionally fed separately. Alternatively, feed based individual dosage forms may be used such as a chewable treat. Alternatively, the antiparasitic compounds of this invention may be administered to animals parenterally, for example, by intraruminal, intramuscular, intravascular, intratracheal, or subcutaneous injection in which the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, propylene glycol, and aqueous parenteral formulations are also used. The active compound or compounds are dissolved or suspended in the parenteral formulation for administration; such formulations generally contain from 0.0005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting arthropods in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1–5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 0.005 to 2.0% weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular compound employed, the compounds of this invention are usually fed at concentrations of between 0.00001 to 0.002% in the feed in order to achieve the desired antiparasitic result.

In using the compounds of this invention, the individual compounds may be prepared and used in that form. Alternatively, mixtures of the individual compounds may be used, or other active compounds not related to the compounds of this invention.

The compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The following examples are provided in order that this invention might be more fully understood; they are not to be construed as limitative of the invention.

EXAMPLE 1

7,13-Bis-O-Trimethylsilyl-5-O-tert.-butyldimethylsilyl-22,23-dihydroavermectin B1a/B2b aglycone Bis (trimethylsilyl) trifluoroacetamide, 50 ml, was added to 11 g of 5-O-tert.-butyldimethylsilyl-22,23-dihydroavermectin B1a/B1b aglycone in 50 ml of dry dimethylformamide. The solution was stirred at 60° C. for 6 hours, cooled to room temperature, diluted with toluene and evaporated under reduced pressure. The residue was dissolved in toluene and evaporated as before. This step was repeated furnishing 12.7 g of 7,13-bis-O-trimethylsilyl-5-O-tert.-butyldimethylsilyl-22,23-dihydroavermectin B1a/B1b aglycone as a yellow foam, 89% purity by HPLC (245 nm), characterized by nuclear magnetic resonance.

EXAMPLE 2

7-O-Trimethylsilyl-5-O-tert.-butyldimethylsilyl-22,23-dihydroavermectin B1a/B1b aglycone Glacial acetic acid, 210 ml, was added to a solution of 7,13-bis-O-trimethylsilyl-5-O-tert.-butyldimethylsilyl-22,23-dihydroavermectin B1a/B1b aglycone, 12.7 g, in 500 ml of tetrahydrofuran followed by the addition of 100 ml of water. The solution was stirred at room temperature, 23° C., for 20 hours and then evaporated to a small volume under reduced pressure. The concentrate was diluted with isopropanol and evaporated again. The concentate was diluted with methylene chloride and neutralized by adding to aqueous sodium bicarbonate with stirring. The layers were separated and the aqueous phase was extracted with methylene chloride. The methylene chloride solutions were combined, extracted with aqueous sodium bicarbonate, dried over anhydrous sodium sulfate and evaporated under reduced pressure providing 11.2 g of a foam solid crude product. The product was purified by flash chromatography on silica gel using hexane-ethyl acetate (95:5 and 90:10) furnishing 7.6 g of 7-O-trimethylsilyl-5-O-tert.-butyldimethylsilyl-22,23-dihydroavermectin B1a/B1b aglycone, 100% purity by HPLC (245 nm), characterized by nuclear magnetic resonance analysis and mass specroscopic [773 m/e, $(M+H)^+$] analyses.

EXAMPLE 3

13-Methylthiomethyl-7-O-trimethylsilyl-5-O-tert.-butyldimethylsilyl-22,23-dihydroavermectin B1a/B1b aglycone Acetic anhydride, 43 ml, was added dropwise over 10 minutes at room temperature, 23° C., to a stirred solution of 7-O-trimethylsilyl-5-O-tert.-butyldimethylsilyl-22,23-dihydroavermectin B1a/B1b aglycone, 7.6 g, in 64 ml of dry dimethylsulfoxide and 13 ml of glacial acetic acid. After 41 hours, the reaction solution was added with stirring to aqueous sodium bicarbonate and ethyl acetate. Stirring was continued for 1 hour and then the layers were separated. The aqueous layer was extracted with ethyl acetate. The ethyl acetate solutions were combined, extracted with aqueous sodium bicarbonate, dried over anhydrous sodium sulfate and evaporated under reduced pressure. The residue was dissolved in toluene and evaporated again furnishing 8.8 g of crude product. The crude was purified by flash chromatography on silica gel using hexane-ethyl acetate (95:5) providing 1.7 g of 13-methylthiomethyl-7-O-trimethylsilyl-5-O-tert.-butyldimethylsilyl-22,23-dihydroavermectin B1a/B1b aglycone, 100% purity by HPLC (245 nm), characterized by nuclear magnetic resonance (3H, S, 2.20 Hz, CH3S-) and mass spectroscopic [839 m/e, $(M+Li)^+$] analyses.

EXAMPLE 4

13-O-Methylthiomethyl-22,23-dihydroavermectin B1a/B1baglycone

A solution of 13-methylthiomethyl-7-O-trimethylsilyl-5-O-tert.-butyldimethylsilyl-22,23-dihydroavermectin B1a/B1b aglycone, 1.7 g, in 73 ml of 0.5% methanolic p-toluenesulfonic acid monohydrate was stirred at room temperature, 23° C. After 30 minutes the solution was poured into aqueous sodium bicarbonate and methylene chloride with stirring. The methylene chloride phase was separated, extracted with aqueous sodium bicarbonate, dried over anhydrous sodium sulfate and evaporated under reduced pressure providing 1.64 g crude product. The crude was purified by flash chromatography on silica gel using methylene chloride-methanol (97:3) furnishing 1.24 g of 13-O-methylthiomethyl-22,23-dihydroavermectin B1a/B1b aglycone, purity 98% by HPLC (245 nm), characterized by nuclear magnetic resonance (3H, S, 2.18 Hz, CH3S-) and mass spectroscopic [653 m/e, (M+Li)+] analyses.

EXAMPLE 5

13-Epi-7,13-bis-O-trimethylsilyl-5-O-tert.-butyldimethylsilyl-22,23-dihydroavermectin B1a/B1b aglycone 13-Epi-5-O-tert.-butyldimethylsilyl-22,23-dihydroavermectin B1a/B1b aglycone, 11.0 g, in 50 ml of dry dimethylformamide was treated with 50 ml of bis (trimethylsilyl) trifluoroacetamide at 60° C. for 2.5 hours by the method of Example 1 furnishing 33.8 g of 13-epi-7,13-bis-O-trimethylsilyl-5-O-tert.-butyldimethylsilyl-22,23-dihydroavermectin B1a/B1b aglycone, 72% purity by HPLC (245 nm), characterized by nuclear magnetic resonance.

EXAMPLE 6

13-Epi-7-O-trimethylsilyl-5-O-tert.-butyldimethylsilyl-22,23-dihydroavermectin B1a/B1b aglycone 13-Epi-7,13-bis-O-trimethylsilyl-5-O-tert.-butyldimethylsilyl-22,23-dihydroavermectin B1a/B1b aglycone, 33.8 g, from Example 5 was treated in 500 ml of tetrahydrofuran, 210 ml of glacial acetic acid and 100 ml of water and purified by the method of Example 2 providing 9.0 g of 13-epi-7-O-trimethylsilyl-5-O-tert.-butyldimethylsilyl-22,23-dihydroavermectin B1a/B1b aglycone, 96% purity by HPLC (245 nm), characterized by nuclear magnetic resonance and mass spectroscopic [773 m/e, (M+Li)+] analyses

EXAMPLE 7

13-Epi-O-methylthiomethyl-7-O-trimethylsilyl-5-O-tert.-butyldimethylsilyl-22,23-dihydroavermectin B1a/B1b aglycone 13-Epi-7-O-trimethylsilyl-5-O-tert.-butyldimethylsilyl-22,23-dihydroavermectin B1a/B1b aglycone, 9.0 g, was treated with 250 ml of dimethylsulfoxide, 10 ml of glacial acetic acid and 56 ml of acetic anhydride and purified by the method of Example 3 furnishing 3.8 g of 13-epi-O-methylthiomethyl-7-O-trimethylsilyl-5-O-tert.-butyldimethylsilyl-22,23-dihydroavermectin B1a/B1b aglycone, 94% purity by HPLC (245 nm), characterized by nuclear magnetic resonance (3H, S, 2.14 Hz, CH3S-) and mass spectroscopic [839 m/e, (M+Li)+] analyses.

EXAMPLE 8

13-Epi-O-methylthiomethyl-22,23-dihydroavermectin B1a/B1b aglycone

13-Epi-O-methylthiomethyl-7-O-trimethylsilyl-5-O-tert.-butyldimethylsilyl-22,23-dihydroavermectin B1a/B1b aglycone, 3.8 g, was treated with 171 ml of 0.5% methanolic p-toluenesulfonic acid hydrate and purified by the method of Example 4 providing 2.2 g of 13-epi-O-methylthiomethyl-22,23-dihydroavermectin B1a/B1b aglycone, 99% purity by HPLC (245 nm), characterized by nuclear magnetic resonance (3H, S, 2.14 Hz, CH3S-) and mass spectroscopic [653 m/e, (M+Li)+] analyses.

EXAMPLE 9

4′,7-Bis-O-Trimethylsilyl-5-O-tert.-butyldimethylsilyl-22,23-dihydroavermectin B1a/B1b monosaccharide 5-O-Tert.-butyldimethylsilyl-22,23-dihydroavermectin B1a/B1b monosaccharide, 7.65 g, in 28 ml of dry dimethylformamide was treated with 28 ml of bis (trimethylsilyl) trifluoroacetamide at 60° C. for 2.5 hours by the method of Example 1 furnishing 8.61 g of 4′,7-bis-O-trimethylsilyl-5-O-tert.-butyldimethylsilyl-22,23-dihydroavermectin B1a/B1b monosaccharide, 64% purity by HPLC (245 nm), characterized by thin layer chromatography and nuclear magnetic resonance.

EXAMPLE 10

7-O-Trimethylsilyl-5-O-tert.-butyldimethylsilyl-22,23-dihydroavermectin B1a/B1b monosaccharide 4′,7-Bis-O-Trimethylsilyl-5-O-tert.-butyldimethylsilyl-22,23-dihydroavermectin B1a/B1b monosaccharide, 8.61 g, from Example 9 was treated with 225 ml of tetrahydrofuran, 95 ml of glacial acetic acid and 44 ml of water and purified by the method of Example 2 providing 5.9 g of 7-O-trimethylsilyl-5-O-tert.-butyldimethylsilyl-22,23-dihydroavermectin B1a/B1b monosaccharide, 96% purity by HPLC (245 nm), characterized by nuclear magnetic resonance and mass spectroscopic [923 m/e, (M+Li)+] analyses.

EXAMPLE 11

4′-O-Methylthiomethyl-7-O-trimethylsilyl-5-O-tert.-butyldimethylsilyl-22,23-dihydroavermectin B1a/B1b monosaccharide 7-O-Trimethylsilyl-5-O-tert. -butyldimethylsilyl-22,23-dihydroavermectin B1a/B1b monosaccharide, 5.8 g, was treated with 139 ml of dimethylsulfoxide, 6.0 ml of glacial acetic acid and 30.3 ml of acetic anhydride and purified by the method of Example 3 furnishing 2.1 g of 4′-O-methylthiomethyl-7-O-trimethylsilyl-5-O-tert.-butyldimethylsilyl-22,23-dihydroavermectin B1a/B1b monosaccharide, 100% purity by HPLC (245 nm), characterized by nuclear magnetic resonance (3H, S, 2.19 Hz, CH3S-) and mass spectroscopic [984 m/e, (M+H+Li)+] analyses.

EXAMPLE 12

4′-O-Methylthiomethyl-22,23-dihydroavermectin B1a/B1b monosaccharide

4′-O-Methylthiomethyl-7-O-trimethylsilyl-5-O-tert.-butyldimethylsilyl-22,23-dihydroavermectin B1a/B1b monosaccharide, 2.1 g, was treated with 81 ml of 0.5% methanolic p-toluenesulfonic acid hydrate and purified by the method of Example 4 providing 1.38 g of 4′-O-methylthiomethyl-22,23-dihydroavermectin B1a/B1b monosaccharide, 100% purity by HPLC (245 nm), characterized by nuclear magnetic resonance (3H, S, 2.19 Hz, CH3S-) and mass spectroscopic [798 m/e, (M+Li)+] analyses.

EXAMPLE 13

4′,7-Bis-O-Trimethylsilyl-5-O-tert.-butyldimethylsilyl avermectin B1a/B1b monosaccharide 5-O-Tert.-butyldimethylsilyl avermectin B1a/B1b monosaccharide, 10.0 g, in 37 ml of dry dimethylformamide was treated with 37 ml of bis (trimethylsilyl) trifluoroacetamide at 60° C. for 2.5 hours by the method of Example 1 furnishing 11.8 g of 4′,7-bis-O-trimethylsilyl-5-O-tert.-butyldimethylsilyl avermectin B1a/B1b monosaccharide characterized by thin layer chromatography and nuclear magnetic resonance.

EXAMPLE 14

7-O-Trimethylsilyl-5-O-tert.-butyldimethylsilyl avermectin B1a/B1b monosaccharide 4',7-Bis-O-Trimethylsilyl-5-O-tert.-butyldimethylsilyl avermectin B1a/B1b monosaccharide, 11.8 g, from Example 13 was treated with 309 ml of tetrahydrofuran, 131 ml of glacial acetic acid and 60 ml of water and purified by the method of Example 2 providing 8.7 g of 7-O-trimethylsilyl-5-O-tert.-butyldimethylsilyl avermectin B1a/B1b monosaccharide, 100% purity by HPLC (245 nm), characterized by thin layer chromatography and nuclear magnetic resonance.

EXAMPLE 15

4'-O-Methylthiomethyl-7-O-trimethylsilyl-5-O-tert.-butyldimethylsilyl avermectin B1a/B1b monosaccharide 7-O-Trimethylsilyl-5-O-tert.-butyldimethylsil yl avermectin B1a/B1b monosaccharide, 5.0 g, was treated with 122 ml of dimethylsulfoxide, 5.3 ml of glacial acetic acid and 26 ml of acetic anhydride and purified by the method of Example 3 furnishing 2.1 g of 4'-O-methylthiomethyl-7-O-trimethylsilyl-5-O-tert.-butyldimethylsilyl avermectin B1a/B1b monosaccharide, 100% purity by HPLC (245 nm), characterized by nuclear magnetic resonance (3H, S, 2.15 Hz, CH3S-) and mass spectroscopic [982 m/e, $(M+H+Li)^+$] analyses.

EXAMPLE 16

4'-O-Methylthiomethyl avermectin B1a/B1b monosaccharide

4'-O-Methylthiomethyl-7-O-trimethylsilyl-5-O-tert.-butyldimethylsilyl avermectin B1a/B1b monosaccharide, 2.2 g, was treated with 84 ml of 0.5% methanolic p-toluenesulfonic acid hydrate and purified by the method of Example 4 providing 1.55 g of 4'-O-methylthiomethyl avermectin B1a/B1b monosaccharide, 99% purity by HPLC (245 nm), characterized by nuclear magnetic resonance (3H, S, 2.18 Hz, CH3S-) and mass spectroscopic [796 m/e, $(M+Li)^+$] analyses.

EXAMPLE 17

7,13-Bis-O-trimethylsilyl-5-O-tert.-butyldimethylsilyl avermectin B1 aglycone

5-O-Tert.-butyldimethylsilyl avermectin B1 aglycone, 16.2 g, in 74 ml of dry dimethylformamide was treated with 74 ml of bis (trimethylsilyl)trifluoroacetamide at 60° C. by the method of Example 1 furnishing 19.8 g of 7,13-bis-O-trimethylsilyl-5-O-tert.-butyldimethylsilyl avermectin B1 aglycone, 98% purity by HPLC (245 nm), characterized by nuclear magnetic resonance and mass spectroscopic [850 m/e, $(M+H+Li)^+$] analyses.

EXAMPLE 18

7-O-Trimethylsilyl-5-O-tert.-butyldimethylsilyl avermectin B1 aglycone 7,13-Bis-O-trimethylsilyl-5-O-tert.-butyldimethylsilyl avermectin B1 aglycone, 19.8 g, was reacted in 500 ml of tetrahydrofuran, 210 ml of glacial acetic acid and 100 ml of water at room temperature, 23° C., and purified by the method of Example 2 providing 18.7 g of 7-O-trimethylsilyl-5-O-tert.-butyldimethylsilyl avermectin B1 aglycone, 100% purity by HPLC (245 nm), and characterized by nuclear magnetic resonance and mass spectroscopic [778 m/e, $(M+H+Li)^+$] analyses.

EXAMPLE 19

13-O-Methylthiomethyl-7-O-trimethylsilyl-5-O-tert.-butyldimethylsilyl avermectin B1 aglycone 7-O-Trimethylsilyl-5-O-tert.-butyldimethylsilyl avermectin B1 aglycone, 7.6 g, is treated with 64 ml of dimethylsulfoxide, 13 ml of glacial acetic acid and 43 ml of acetic anhydride and is purified by the method of Example 3 furnishing 13-O-methylthiomethyl-7-O-trimethylsilyl-5-O-tert.-butyldimethylsilyl avermectin B1 aglycone.

EXAMPLE 20

13-O-Methylthiomethyl avermectin B1 aglycone

13-O-Methylthiomethyl-7-O-trimethylsilyl-5-O-tert.-butyldimethylsilyl avermectin B1 aglycone, 3.8 g, is treated with 171 ml of 0.5% methanolic p-toluenesulfonic acid hydrate at room temperature, 23° C., for 30 minutes and is purified by the method of Example 4 providing 13-O-methylthiomethyl avermectin B1 aglycone.

EXAMPLE 21

4",7-Bis-O-trimethylsilyl-5-O-tert.-butyldimethylsilyl-22,23-dihydroavermectin B1

5-O-Tert.-butyldimethylsilyl-22,23-dihydroavermectin B1, 8.96 g, in 28 ml of dry dimethylformamide is treated with 28 ml of bis (trimethylsilyl) trifluoroacetamide at 60° C. for 2.5 hours by the method of Example 1 furnishing 4",7-bis-O-trimethylsilyl-5-O-tert.-butyldimethylsilyl-22,23-dihydroavermectin B1.

EXAMPLE 22

7-O-Trimethylsilyl-5-O-tert.-butyldimethylsilyl-22,23-dihydro avermectin B1

4",7-Bis-O-trimethylsilyl-5-O-tert.-butyldimethylsilyl-22,23-dihydroavermectin B1, 10.1 g, from Example 21 is treated with 225 ml of tetrahydrofuran, 95 ml of glacial acetic acid and 44 ml of water at room temperature, 23° C., and purified by the method of Example 2 providing 7-O-trimethylsilyl-5-O-tert.-butyldimethylsilyl-22,23-dihydroavermectin B1.

EXAMPLE 23

4"-O-Methylthiomethyl-7-O-trimethylsilyl-5-O-tert.-butyldimethylsilyl-22,23-dihydroavermectin B1

7-O-Trimethylsilyl-5-O-tert.-butyldimethylsilyl-22,23-dihydroavermectin B1, 6.8 g, is treated with 139 ml of dimethylsulfoxide, 6.0 ml of glacial acetic acid and 30.3 ml of acetic anhydride and is purified by the method of Example 3 furnishing 4"-O-methylthiomethyl-7-O-trimethylsilyl-5-O-tert.-butyldimethylsilyl-22,23-dihydroavermectin B1.

EXAMPLE 24

4"-O-Methylthiomethyl-22,23-dihydroavermectin B1

4"-O-Methylthiomethyl-7-O-trimethylsilyl-5-O-tert.-butyldimethylsilyl-22,23-dihydroavermectin B1, 2.5 g, from Example 23 is treated with 81 ml of 0.5% methanolic p-toluenesulfonic acid hydrate at room temperature, 23° C., for 30 minutes and is purified by the method of Example 4 providing 4''-O-methylthiomethyl-22,23-dihydroavermectin B1.

EXAMPLE 25

4'',7-Bis-O-trimethylsilyl-5-O-tert.-butyldimethylsilyl avermectin B1

5-O-Tert.-butyldimethylsilyl avermectin B1, 8.96 g, in 28 ml of dry dimethylformamide is treated with 28 ml of bis (trimethylsilyl) trifluoroacetamide at 60° C. for 2.5 hours by the method of Example 1 furnishing 4'',7-bis-O-trimethylsilyl-5-O-tert.-butyldimethylsilyl avermectin B1.

EXAMPLE 26

7-O-Trimethylsilyl-5-O-tert.-butyldimethylsilyl avermectin B1

4'',7-Bis-O-trimethylsilyl-5-O-tert.-butyldimethylsilyl-avermectin B1, 10.1 g, from Example 25 is treated with 225 ml of tetrahydrofuran, 95 ml of glacial acetic acid and 44 ml of water at room temperature, 23° C., and is purified by the method of Example 2 providing 7-O-trimethylsilyl-5-O-tert.-butyldimethylsilyl avermectin B1.

EXAMPLE 27

4''-O-Methylthiomethyl-7-O-trimethylsilyl-5-O-tert.-butyldimethylsilyl avermectin B1

7-O-Trimethylsilyl-5-O-tert.-butyldimethylsilyl avermectin B1, 6.8 g, from Example 26 is treated with 139 ml of dimethylsulfoxide, 6.0 ml of glacial acetic acid and 30.3 ml of acetic anhydride and is purified by the method of Example 3 furnishing 4''-O-methylthiomethyl-7-O-trimethylsilyl-5-O-tert.-butyldimethylsilyl avermectin B1.

EXAMPLE 28

4''-O-Methylthiomethyl avermectin B1

4''-O-Methylthiomethyl-7-O-trimethylsilyl-5-O-tert.-butyldimethylsilyl avermectin B1, 2.5 g, from Example 27 is treated with 81 ml of 0.5% methanolic p-toluenesulfonic acid hydrate at room temperature, 23° C., for 30 minutes and is purified by the method of Example 4 providing 4''-O-methylthiomethyl-22,23-dihydroavermectin B1.

EXAMPLE 29

13-O-Methylthiomethyl-10,11,22,23-tetrahydroavermectin B1 aglycone

13-O-Methylthiomethyl-22,23-dihydroavermectin B1 aglycone, 5.0 g, from Example 4 and 0.5 g of 5% palladium on charcol in 50 ml of ethanol is stirred at room temperature, 23° C., under an atmosphere of hydrogen contained in a balloon just until no more starting aglycone remains as determined by TLC AND HPLC. Celite is added with stirring to the reaction mixture and the resulting insolubles are removed by filtering through a bed of Celite. The filtrate is concentrated under reduced pressure leaving a crude product as a solid residue. The product is purified by flash chromatography on a column of silica gel using methylene chloride-ethyl acetate-methanol (90:10:0.5) furnishing 13-O-methylthiomethyl-10,11,22,23-tetrahydroavermectin B1 aglycone.

EXAMPLE 30

13-O-Methylthiomethyl-11-bromo-10-hydroxy-10,11,22,23-tetrahydroavermectin B1 aglycone N-Bromoacetamide, 1.83 g (13.2 mMole), is added to a solution of 13-methylthiomethyl-22,23-dihydroavermectin B1 aglycone, 8.0 g (11.8 mMole), in 200 ml of 10% water in acetone. The mixture is stirred at room temperature, 23° C., in the dark for 3.5 hours as determined by TLC and HPLC. The mixture is poured into 5% aqueous sodium bicarbonate and methylene chloride. with stirring. The phases are separated and the aqueous phase is extracted with methylene chloride. The methylene chloride solutions are combined, extracted with 5% aqueous sodium bicarbonate, dried over anhydrous sodium sulfate and evaporated under reduced pressure providing 13-O-methylthiomethyl-11-bromo-10-hydroxy-10,11,22,23-tetrahydroavermectin B1 aglycone as a impure product which is used immediately for debromination, see Example 31.

EXAMPLE 31

13-O-Methylthiomethyl-10-hydroxy-10,11,22,23-tetrahydroavermectin B1 aglycone

Tributyltin hydride, 15.5 ml, is added to a solution of 13-O-methylthiomethyl-11-bromo-10-hydroxy-10,11,22,23-tetrahydroavermectin B1 aglycone, 8.9 g, from Example 30 and 2,2'-azobis(2-methylpropionitrile), 400 mg, in 102 ml of dry toluene with stirring under an atmosphere of nitrogen and is immediately placed into a preheated, 85° C., oil bath. Stirring is continued for 2 hours as determined by TLC and HPLC. After cooling, the reaction solution is poured into a mixture of 5% aqueous sodium bicarbonate and methylene chloride with stirring for 60 minutes. The phases are separated and the aqueous phase is extracted with methylene chloride. The methylene chloride solutions are combined, extracted with aqueous sodium bicarbonate, dried over anhydrous sodium sulfate and evaporated under reduced pressure leaving a crude product as a viscous residue. The product is purified by flash chromatography on a column of silica gel using methylene chloride-methanol (97:3) providing 13-O-methylthiomethyl-10-hydroxy-10,11,22,23-tetrahydroavermectin B1 aglycone.

EXAMPLE 32

13-O-Methylthiomethyl-10-hydroxy-5-O-tert.-butyldimethylsilyl-10,11,22,23-tetrahydroavermectin B1 aglycone 5-O-Tert.-butyldimethylsilyl chloride, 4.06 g, is added to a solution of 13-O-methylthiomethyl-10-hydroxy-10,11,22,23-tetrahydroavermectin B1 aglycone, 6.29 g, and imidazole, 3.67 g, in 100 ml of dry dimethylformamide with stirring at room temperature, 23° C. After stirring for 60 minutes, the reaction solution is added to 5% aqueous sodium bicarbonate and methylene chloride. The mixture is stirred for 20 minutes. The phases are separated and the aqueous phase is extracted with methylene chloride. The methylene chloride solutions are combined, extracted with 5% aqueous sodium bicarbonate, dried over anhydrous sodium sulfate and evaporated under reduced pressure leaving a crude product as a viscous residue. The product is purified by flash chromatography on a column of silica gel using methylene chloride-methanol (97:3) providing 13-O-methylthiomethyl-10-hydroxy-5-O-tert.-butyldimethylsilyl-10,11,22,23-tetrahydroavermectin B1 aglycone.

EXAMPLE 33

13-O-Methylthiomethyl-10-fluoro-5-O-tert.-butyldimethylsilyl-10,11,22,23-tetrahydroavermectin B1 aglycone Diethylaminosulfur trifluoride, 1.2 ml (9.0 mMole), in 36 ml of dry methylene chloride is added dropwise to a cold, −65° C., solution of 13-O-methyl-thiomethyl-10-hydroxy-5-O-tert.-butyldimethylsilyl-10,11,22,23-tetrahydroavermectin B1 aglycone, 6.1 g (7.5 mMole), in 37 ml of dry methylene chloride with stirring under a dry nitrogen atmosphere. The reaction solution is stirred at −65° C. for 90 minutes and then is added to 5% aqueous sodium bicarbonate and methylene chloride. The mixture is stirred for 20 minutes. The phases are separated and the aqueous phase is extracted with methylene chloride. The methylene chloride solutions are combined, extracted with 5% aqueous sodium bicarbonate, dried over anhydrous sodium sulfate and evaporated under reduced pressure leaving a crude product as a viscous residue. The product is purified by flash chromatography on a column of silica gel using hexane-acetone (90:10) providing 13-O-methylthiomethyl-10-fluoro-5-O-tert.-butyldimethylsilyl-10,11,22,23-tetrahydroavermectin B1 aglycone.

EXAMPLE 34

13-O-Methylthiomethyl-10-fluoro-10,11,22,23-tetrahydroavermectin B1 aglycone 3.5 ML of a mixture containing commercial anhydrous hydrogen fluoride-pyridine (approx. 70:30), pyridine and tetrahydrofuran (43:50:80), is added to a solution of 13-O-methylthiomethyl-10-fluoro-5-O-tert.-butyldimethylsilyl-10,11,22,23-tetrahydroavermectin B1 aglycone, 3.5 g, in 3.5 ml of dry pyridine with stirring at room temperature, 23° C. After stirring for 16 hours, the reaction solution is added to 5% aqueous sodium bicarbonate and methylene chloride. The mixture is stirred for 20 minutes. The phases are separated and the aqueous phase is extracted with methylene chloride. The methylene chloride solutions are combined, extracted with 5% aqueous sodium bicarbonate, dried over anhydrous sodium sulfate and evaporated under reduced pressure leaving a crude product as a viscous residue. The product is purified by flash chromatography on a column of silica gel using methylene chloride-methanol (99:1 to 97:3) providing 13-O-methylthiomethyl-10-fluoro-10,11,22,23-tetrahydroavermectin B1 aglycone.

What is claimed is:

1. A compound having the formula

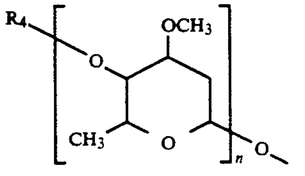

-continued

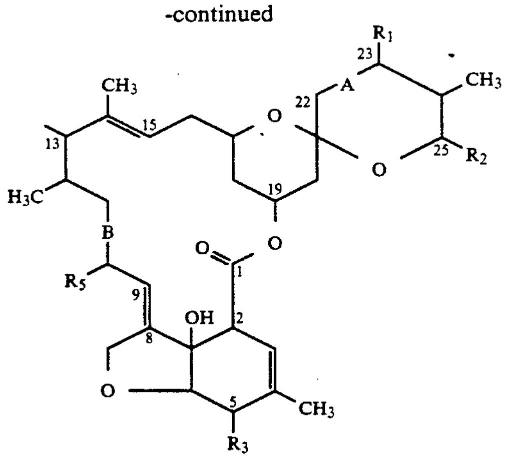

where:
n is 0;
A is single or double bond;
$R_1$ is present only when A is a single bond and is H, OH, =O, =$NOCH_3$ or halogen;
$R_2$ is $C_1$-$C_6$ alkyl, $C_2$-$C_6$ alkenyl, $C_3$-$C_8$ cycloalkyl, $C_4$-$C_8$ cycloalkenyl, phenyl, furyl or thienyl;
$R_3$ is OH or =NOH;
B is a single or double bond;
$R_5$ is present only when B is a single bond and is H, OH or halogen;
$R_4$ is

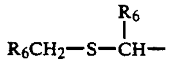

and $R_6$ is hydrogen or $C_1$-$C_3$ alkyl.

2. A compound of claim 1 where
A is a single bond;
$R_1$ is H, OH or =O;
$R_2$ is $C_1$-$C_6$ alkyl or $C_3$-$C_8$ cycloalkyl;
$R_3$ is OH;
B is a double bond; and
$R_6$ is hydrogen or methyl.

3. A compound of claim 2 where
A is a single bond;
$R_1$ is H or OH;
$R_2$ is $C_3$-$C_4$ alkyl or $C_5$-$C_6$ cycloalkyl;
$R_3$ is OH;
B is a double bond; and
$R_6$ is hydrogen.

4. A compound of claim 1 which is selected from the group consisting of
13-O-Methylthiomethyl-22,23-dihydroavermectin B1 aglycone;
13-Epi-O-methylthiomethyl-22,23-dihydroavermectin B1 aglycone;
13-O-Methylthiomethyl avermectin B1 aglycone;
13-O-Methylthiomethyl-10,11,22,23-tetrahydroavermectin B1 agylcone;
13-O-Methylthiomethyl-10-hydroxy-10,11,22,23-tetrahydroavermectin B1 aglycone; and
13-O-Methylthiomethyl-10-fluoro-10,11,22,23-tetrahydro avermectin B1 aglycone.

5. A method for the treatment of parasitic infections in animals which comprise administering to such animals infected with parasites an effective amount of a compound of claim 1.

6. A method for the treatment of parasitic infections of plants, soil or premises which comprise applying to such plants, soil or premises infected with parasites an effective amount of a compound of claim 1.

7. A composition useful for the treatment of parasitic infections of animals or parasitic infestations of plants, soil or premises which comprise an inert carrier and an effective amount of a compound of claim 1.

* * * * *